United States Patent [19]
Chambers et al.

[11] Patent Number: 5,998,415
[45] Date of Patent: Dec. 7, 1999

[54] BICYCLIC HETEROARYL-ALKYLENE-(HOMO)PIPERAZINONES AND THIONE ANALOGUES THEREOF, THEIR PREPARATION, AND THEIR USE OF AS SELECTIVE AGONISTS OF 5-HT$_1$-LIKE RECEPTORS

[75] Inventors: Mark Stuart Chambers, Puckeridge; Sarah Christine Hobbs, Great Dunmow; Leslie Joseph Street, Harlow, all of United Kingdom

[73] Assignee: Merck Sharp & Dohme Ltd., Hoddesdon, United Kingdom

[21] Appl. No.: 09/065,020

[22] PCT Filed: Oct. 28, 1996

[86] PCT No.: PCT/GB96/02624

§ 371 Date: Apr. 17, 1998

§ 102(e) Date: Apr. 17, 1998

[87] PCT Pub. No.: WO97/16446

PCT Pub. Date: May 9, 1997

[30] Foreign Application Priority Data

Nov. 2, 1995 [GB] United Kingdom .................. 9522473
Nov. 22, 1995 [GB] United Kingdom .................. 9523907

[51] Int. Cl.$^6$ ............ A61K 31/495; C07D 403/06; C07D 403/14

[52] U.S. Cl. ............ 514/253; 514/218; 544/263; 544/366; 544/367; 544/369; 544/370; 544/371; 544/373

[58] Field of Search ............ 544/366, 367, 544/373, 369; 514/253

[56] References Cited

U.S. PATENT DOCUMENTS 5,808,064  9/1998  Chen et al. .................. 544/132

FOREIGN PATENT DOCUMENTS

| | | |
|---|---|---|
| 0 438 230 A2 | 7/1991 | European Pat. Off. . |
| 0 494774 A1 | 7/1992 | European Pat. Off. . |
| 0 497 512 A2 | 8/1992 | European Pat. Off. . |
| 0 548 813 A1 | 6/1993 | European Pat. Off. . |
| 944443 | 12/1963 | United Kingdom . |
| 1075156 | 7/1967 | United Kingdom . |
| 91/18897 | 12/1991 | WIPO . |
| 92/17475 | 10/1992 | WIPO . |
| 94/21630 | 9/1994 | WIPO . |
| 95/29911 | 6/1995 | WIPO . |
| 95/321966 | 11/1995 | WIPO . |
| 96/16056 | 5/1996 | WIPO . |
| 96/23785 | 8/1996 | WIPO . |

*Primary Examiner*—Emily Bernhardt
*Attorney, Agent, or Firm*—James L. McGinnis; David L. Rose; Philippe L. Durette

[57] ABSTRACT

A class of piperazinones, homopiperazinones and thione analogues thereof, substituted at the 1-position by an optionally substituted alkenyl, alkynyl, aryl-alkyl or heteroaryl-alkyl moiety, and linked at the 4-position via an alkylene spacer to a fused bicyclic heteroaromatic moiety, typically indolyl, are selective agonists of 5-HT$_1$-like receptors, being potent agonists of the human 5-HT$_{1D\alpha}$ receptor subtype while possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, while eliciting fewer side-effects, notably adverse cardiovascular events, than those associated with non-subtype-selective 5-HT$_{1D}$ receptor agonists.

12 Claims, No Drawings

BICYCLIC HETEROARYL-ALKYLENE-(HOMO)PIPERAZINONES AND THIONE ANALOGUES THEREOF, THEIR PREPARATION, AND THEIR USE OF AS SELECTIVE AGONISTS OF 5-HT$_1$-LIKE RECEPTORS

The present invention relates to a class of substituted piperazinones, homopiperazinones and thione analogues thereof which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted piperazinone and related heterocyclic derivative provided by the present invention.

In EP-A-0548813 is described a series of alkyoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 replacing the substituted piperazine moiety with a differently substituted piperazinone or related heterocyclic moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the substituted piperazinone and related heterocyclic derivatives provided by the present invention.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

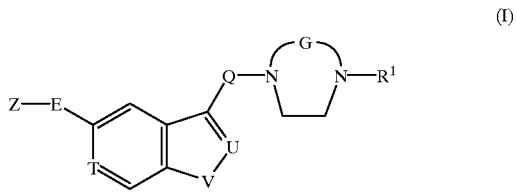

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (Za), (Zb), (Zc) or (Zd):

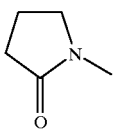
(Za)

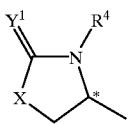
(Zb)

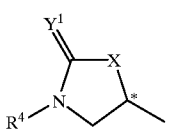
(Zc)

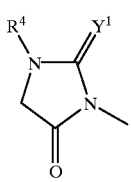
(Zd)

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

$Y^1$ represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—$R^2$;

V represents oxygen, sulphur or N—$R^3$;

G represents a group of formula (Ga), (Gb), (Gc) or (Gd):

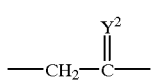
(Ga)

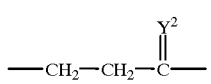
(Gb)

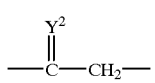
(Gc)

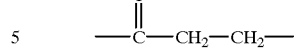
(Gd)

in which $Y^2$ represents oxygen or sulphur;

$R^1$ represents $C_{3-6}$ alkenyl, $C_{3-6}$ alkynyl, aryl($C_{1-6}$)alkyl or heteroaryl($C_{1-6}$)alkyl, any of which groups may be optionally substituted;

$R^2$, $R^3$ and $R^4$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring.

The present invention also provides a compound of formula I as defined above, or a salt or prodrug thereof, wherein Q represents a straight or branched alkylene chain containing from 1 to 6 carbon atoms, optionally substituted in any position by a hydroxy group; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^1$, $R^5$ or $R^6$ represents aryl($C_{1-6}$)alkyl or heteroaryl($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyltetrazolyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$) alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl $(C_{1-6})$alkyl, $C_{1-6}$ alkoxy, $C_{2-6}$ alkoxycarbonyl and $C_{1-6}$ alkylaminocarbonyl. Typical substituents include methyl, benzyl, methoxy, methoxycaronyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyrindinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs,* ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethyl-propylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include propylene, butylene, 2-hydroxypropylene, 2-hydroxymethyl-propylene, 2-fluoropropylene or 2-fluoromethyl-propylene, especially propylene.

The compound of formula I in accordance with the present invention is suitably an indole, benzofuran or benzthiophene derivative of formula IA, an indazole derivative of formula IB, or a pyrrolo[2,3-c]pyridine derivative of formula IC:

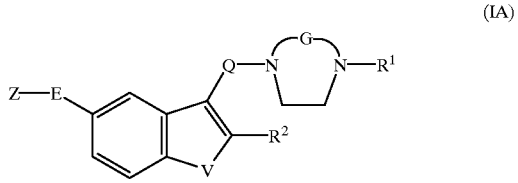

(IA)

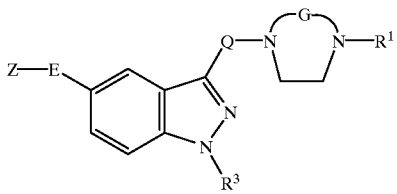

(IB)

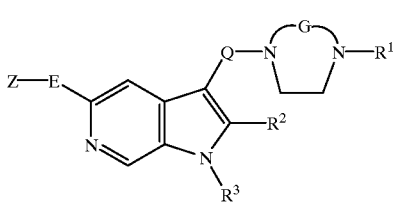

(IC)

wherein Z, E, Q, V, G, $R^1$, $R^2$ and $R^3$ are as defined above. Preferably, the compounds according to the invention are indole or pyrrolo[2,3-c]pyridine derivatives of formula ID:

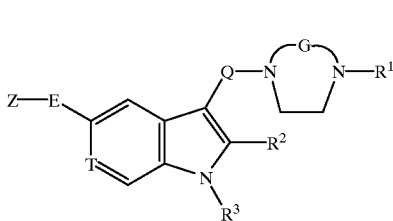

(ID)

wherein Z, E, Q, T, G, $R^1$, $R^2$ and $R^3$ are as defined above, in particular wherein $R^2$ and $R^3$ are both hydrogen.

Suitable values for the substituent $R^1$ include allyl, dimethylallyl, butenyl, propargyl, benzyl, phenylethyl, phenylpropyl, furylmethyl, thienylmethyl, imidazolylmethyl and pyridylmethyl, any of which groups may be optionally substituted by one or more substituents selected typically from halogen, cyano, triazolyl, tetrazolyl, $C_{1-6}$ alkyl-tetrazolyl, $C_{1-6}$ alkoxy, amino, di($C_{1-6}$)alkylamino, di($C_{1-6}$)alkyl-aminomethyl, $C_{2-6}$ alkylcarbonylamino, $C_{2-6}$ alkoxycarbonylamino, C-($C_{1-6}$)alkyl-N-($C_{2-6}$) alkoxycarbonylamino, $C_{1-6}$ alkylsulphonylamino, aminocarbonylamino, aminocarbonyl, $C_{1-6}$ alkylaminocarbonyl, di($C_{1-6}$)alkylaminocarbonyl, aminosulphonyl and $C_{1-6}$ alkylaminosulphonylmethyl.

Particular values of $R^1$ include allyl, dimethylallyl, butenyl, propargyl, benzyl, fluorobenzyl, difluorobenzyl, cyanobenzyl, tetrazolyl-benzyl, methyltetrazolyl-benzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, phenylethyl (including 1-phenylethyl and 2-phenylethyl), fluoro-phenylethyl, difluoro-phenylethyl, cyano-phenylethyl, triazolyl-phenylethyl, amino-phenylethyl, dimethylamino-phenylethyl, acetylamino-phenylethyl, methoxycarbonylamino-phenylethyl, (N-methyl-N-methoxycarbonyl(amino-phenylethyl, aminocarbonylamino-phenylethyl, phenylpropyl (including 2-phenylpropyl and 3-phenylpropyl), furylmethyl, thienylmethyl, imidazolylmethyl, pyridylmethyl and aminopyridylmethyl.

More particularly, $R^1$ may suitably represent benzyl, 1-phenylethyl, 2-phenylethyl, fluoro-phenylethyl, difluoro-phenylethyl or 2-phenylpropyl.

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylpehnyl), benzyl and phenethyl.

Suitably, the substituent Z represents hydrogen, fluoro, cyano, hydroxy, methoxy, ethoxy, benzyloxy, methylaminocarbonyloxy, cyano-methoxy, aminocarbonyl-methoxy, methylsulphonyl, aminosulphonyl, N-methylaminosulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered heteroaromatci ring as specified above.

In a particular embodiment, Z represents $—SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and $Y^1$ both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thizaole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Suitably, the moiety G represents a group of formula (Ga) or (Gb) as defined above, especially (Ga).

Suitably, $Y^2$ is oxygen.

A particular sub-class of compounds according to the invention is represented by the compounds of formula IIA, and salts and prodrugs thereof:

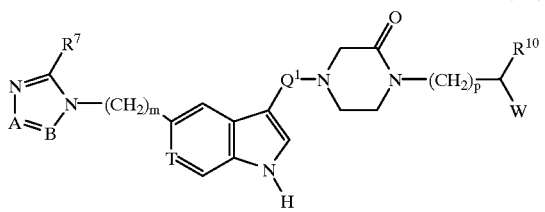

(IIA)

wherein
m is zero, 1, 2 or 3, preferably zero or 1;
p is zero, 1 or 2;
$Q^1$ represents a straight or branched alkylene chain containing from 2 to 5 carbon atoms, optionally substituted in any position by a hydroxy group;
T represents nitrogen or CH;
A represent nitrogen or CH;
B represent nitrogen or C—$R^8$;
$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;
W represents a group of formula (Wa), (Wb) or (Wc):

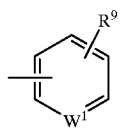

(Wa)

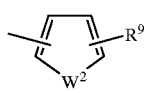

(Wb)

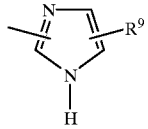

(Wc)

in which
$W^1$ represents CH or nitrogen;
$W^2$ represents oxygen, sulphur, NH or N-methyl;
$R^9$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$) alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and
$R^{10}$ represents hydrogen or $C_{1-3}$ alkyl.

Suitably, $Q^1$ represents a straight or branched 3 or 4 carbon alkylene chain, optionally substituted in any position by a hydroxy group. Particular alkylene chains for $Q^1$ include propylene, butylene, 2-hydroxypropylene and 2-(hydroxymethyl)-propylene, especially propylene.

Particular values of $R^7$ and $R^8$ include hydrogen, methyl, ethyl, benzyl and amino, especially hydrogen.

Particular values of $R^9$ include hydrogen, fluoro, cyano, triazolyl, tetrazolyl, methyl-tetrazolyl, methoxy, amino, dimethylaminomethyl, acetylamino, aminocarbonylamino, methylaminocarbonyl and aminosulphonyl, especially hydrogen and fluoro.

Particular values of $R^{10}$ include hydrogen and methyl.

Another sub-class of compounds according to the invention is represented by the compounds of formula IIB, and salts and prodrugs thereof:

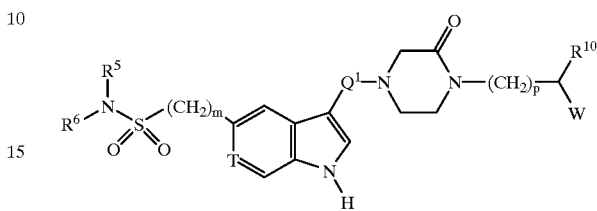

(IIB)

wherein
m, p, $Q^1$, T, W and $R^{10}$ are as defined with reference to formula IIA above; and
$R^5$ and $R^6$ are as defined with reference to formula I above.

Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC, and salts and prodrugs thereof:

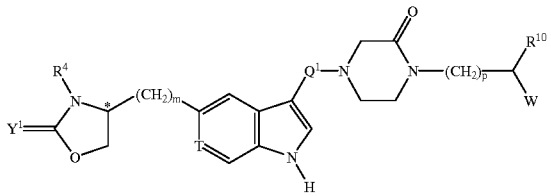

(IIC)

wherein the asterisk * denotes a chiral centre;
m, p, $Q^1$, T, W and $R^{10}$ are as defined with reference to formula IIA above; and
$R^4$ and $Y^1$ are as defined with reference to formula I above.

Particular values of $R^4$ in relation to formula IIC include hydrogen and methyl, especially hydrogen.

Preferably, $Y^1$ in formula IIC is oxygen.

Preferably, the chiral centre denoted by the asterisk * in formula IIC is in the (S) configuration.

In a particular aspect of the compounds of formulae IIA, IIB and IIC above, the substituent $R^{10}$ represents hydrogen.

Specific compounds within the scope of the present invention include:

1-benzyl-4-[3-(5-(1,2,4-triazol-4-yl)-1H-indol-3-yl)propyl] piperazin-2-one;
1-(2-phenylethyl)-4-[3-(5-(1,2,4-triazol-4-yl)-1H-indol-3-yl)propyl]piperazin-2-one;
1-[2-(3-fluorophenyl)ethyl]-4-[3-(5-(1,2,4-triazol-4-yl)-1H-indol-3-yl)propyl]piperzin-2-one;
1-[2-(3,4-difluorophenyl)ethyl]-4-[3-(5-(1,2,4-triazol-4-yl)-1H-indol-3-yl)propyl]piperazin-2-one;
1-benzyl-4-[3-(5-(1,2,4-triazol-4-yl)-1H-indol-3-yl)propyl] piperazin-2-thione;
1-(2-phenylpropyl)-4-[3-(5-(1,2,4-traizol-4-yl)-1H-indol-3-yl)propyl]piperazin-2-one;

1-(1-phenylethyl)-4-[3-(5-(1,2,4-triazol-4-yl)-1H-indol-3-yl)propyl]piperazin-2-one;

1-(2-phenylpropyl)-4-[3-(5-(1,2,4-triazol-4-yl)-1H-indol-3-yl)propyl]piperazin-3-one;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such material as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises attachment of the $R^1$ moiety to a compound of formula III:

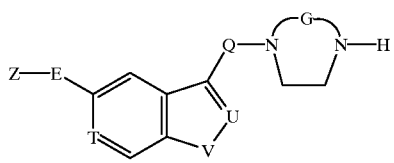

(III)

wherein Z, E, Q, T, U, V and G areas defined above; by conventional means including N-alkylation.

Attachment of the $R^1$ moiety to the compounds of formula III may conveniently be effected by standard alkylation techniques. One example thereof comprises treatment with an alkenyl halide such as 4-bromobut-1-ene, 4-bromo-2-methylbut-2-ene or allyl bromide, an alkynyl halide such as propargyl bromide, or an aryl($C_{1-6}$)alkyl or heteroaryl($C_{1-6}$)alkyl halide such as benzyl iodide, typically under basic conditions, e.g. sodium hydride in N,N-dimethylformamide.

Where G in the compounds of formula I represents a group of formula (Gc) or (Gd) as defined above, the $R^1$ moiety may conveniently be attached by reductive alkylation. This approach suitably comprises treating the required compound of formula III with the appropriate aldehyde, e.g. 2-phenylpropionaldehyde, in the presence of a reducing agent such as sodium cyanoborohydride.

The compounds of formula III above wherein T represents CH, U represents C—$R^2$ and V represents N—$R^3$, corresponding to the indole derivatives of formula ID as defined above wherein T represents CH and $R^1$ is hydrogen, may be prepared by a process which comprises reacting a compound of formula IV:

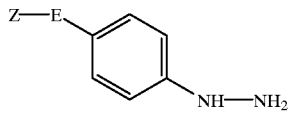

(IV)

wherein Z and E are as defined above; with a compound of formula V, or a carbonyl-protected form thereof:

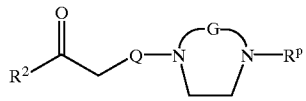

(V)

wherein Q, G and $R^2$ are as defined above, and $R^P$ represents an amino-protecting group; followed, where required, by N-alkylation by standard methods to introduce the moiety $R^3$; with subsequent removal of the amino-protecting group $R^P$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group $R^P$ in the compounds of formula V, especially those compounds wherein G represents a group of formula (Gc) or (Gd), is suitably a carbamoyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

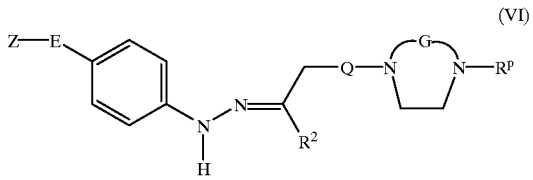

(VI)

wherein Z, E, Q, G, $R^2$ and $R^P$ are defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII: group, this group may condense with the carbonyl moiety in compounds V and IX, whereby the carbonyl moiety is protected in the form of a cyclic hemiacetal.

As with that between compounds IV and V, the Fischer reaction between compounds IV and IX may be carried out in a single step, or may proceed via an initial non-cyclising step at a lower temperature to give an intermediate of formula X:

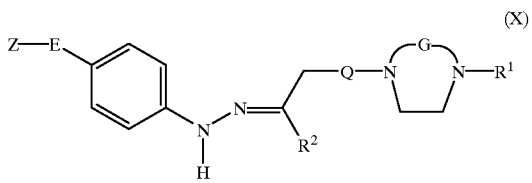

(X)

wherein Z, E, Q, G, $R^1$ and $R^2$ are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

(XI)

wherein G and $R^1$ are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

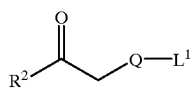

(VII)

(VIII)

Q, G, $R^2$ and $R^P$ are as defined above, and $L^1$ represents a suitable leaving group.

The leaving group $L^1$ is suitably a halogen atom, e.g. chlorine or bromine.

Where $L^1$ represents a halogen atom, the reaction between compounds VII and VIII is conveniently effected by stirring the reactants under basic conditions in a suitable solvent, for example sodium carbonate in 1,2-dimethoxyethane, typically in the presence of sodium iodide.

The compounds according to the invention wherein T represents CH, U represents C—$R^2$ and V represents N—$R^3$—i.e. the indole derivatives of formula ID as defined above wherein T represents CH—may alternatively be prepared by a process which comprises reacting a compound of formula IV as defined above with a compound of formula IX, or a carbonyl-protected form thereof:

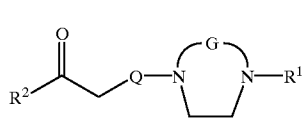

(IX)

wherein Q, G, $R^1$ and $R^2$ are as defined above; under conditions analogous to those described above for the reaction between compounds IV and V; followed, where required, by N-alkylation by standard methods to introduce the moiety $R^3$.

As for the compounds of formula V, suitable carbonyl-protected forms of the compounds of formula IX include the dimethyl acetal or ketal derivatives. Where the alkylene chain Q is substituted by a hydroxy

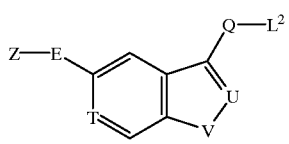

(XII)

wherein Z, E, Q, T, U and V are as defined above, and $L^2$ represents a suitable leaving group; followed by removal of the amino-protecting group $R^P$.

Similarly, the compounds of formula I as defined above may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XII and compound VIII or XI is conveniently carried out in a suitable solvent such as 1,2-dimethoxyethane or isopropyl alcohol, optionally in the presence of a cosolvent such as acetonitrile, typically in the presence of a base such as sodium carbonate or potassium carbonate, and optionally with the addition of sodium iodide.

In one representative approach, the compounds of formula XII wherein T and U both represent CH, V represents NH and L² represents a mesyloxy or tosyloxy group may be prepared by the sequence of steps illustrated in the following reaction scheme (cf. Larock and Yum, *J. Am. Chem. Soc.,* 1991, 113, 6689):

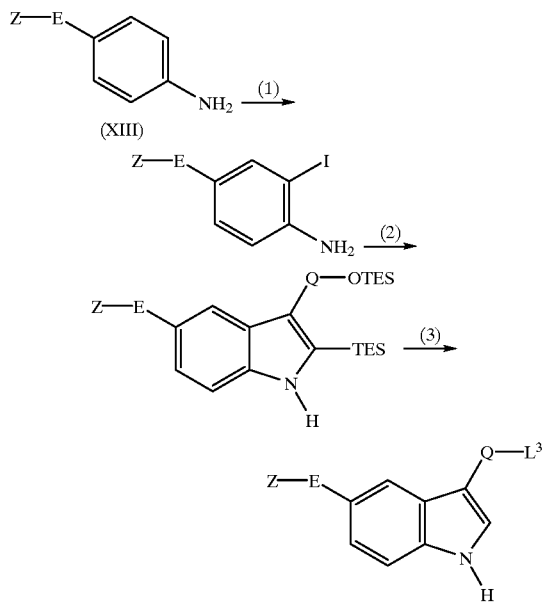

wherein Z, E and Q are as defined above, L³ represents mesyloxy or tosyloxy, and TES is an abbreviation for triethylsilyl.

In Step 1 of the reaction scheme, the aniline derivative XIII is treated with iodine monochloride, typically in methanol or acetonitrile, in order to introduce an iodine atom ortho to the amine moiety. Step 2 involves a palladium-mediated coupling reaction with the protected acetylene derivative TES—C≡C—Q—OTES, typically using palladium acetate and triphenylphosphine in the presence of lithium chloride and sodium carbonate, suitably in N, N-dimethylformamide at an elevated temperature. This is followed in Step 3 by removal of the TES moiety, typically by treatment with hydrochloric acid; followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula XII wherein T and U both represent CH, V represents NH, Q represents a propylene chain and L² represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative IV or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a further procedure, the compounds of formula III above wherein T represents CH, U represents nitrogen and V represents N—R³, corresponding to the indazole derivatives of formula IB as defined above wherein R¹ is hydrogen, may be prepared by a process which comprises cyclising a compound of formula XIV:

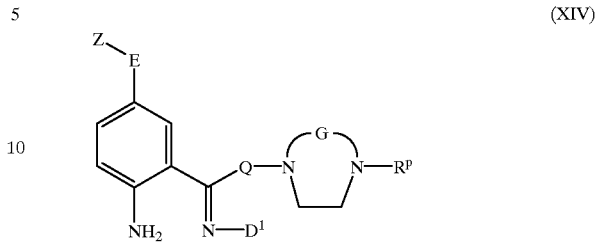

wherein Z, E, Q, G and $R^p$ are as defined above, and $D^1$ represents a readily displaceable group; followed, wherein required, by N-alkylation by standard methods to introduce the moiety $R^3$; with subsequent removal of the amino-protecting group $R^p$.

Similarly, the compounds of formula I wherein T represents CH, U represents nitrogen and V represents N—R³— i.e. the indazole derivatives of formula IB as defined above—may be prepared by a process which comprises cyclising a compound of formula XV:

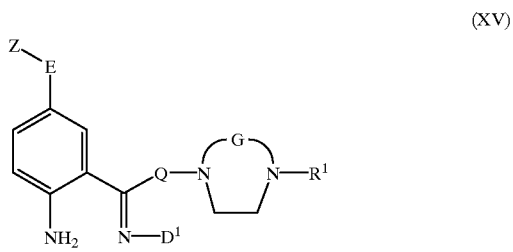

in which Z, E, Q, G, $R^1$ and $D^1$ are as defined above; followed, where required, by N-alkylation by standard methods to introduce the moiety $R^3$.

The cyclisation of compounds XIV and XV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIV and XV suitably represents a $C_{1-4}$ alkanoyloxy group, preferably acetoxy. Where $D^1$ represents acetoxy, the desired compound of formula XIV or XV may be conveniently prepared by treating a carbonyl compound of formula XVI:

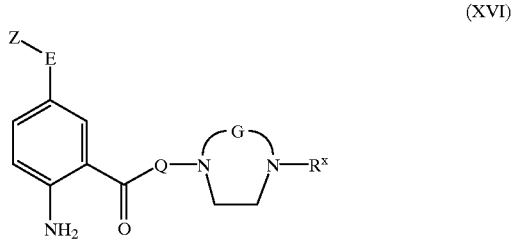

wherein Z, E, Q and G are as defined above, and $R^x$ corresponds to the group $R^1$ as defined above, or $R^x$ represents an amino-protecting group as defined for $R^p$; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XVI may conveniently be prepared by ozonolysis of the corresponding indole derivative of formula XVII:

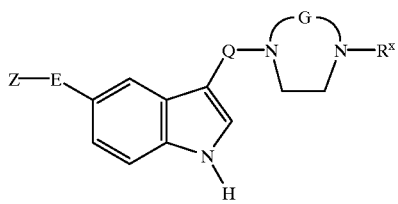
(XVII)

wherein Z, E, Q, G and $R^x$ are as defined above; followed by a reductive work-up, advantageously using dimethylsulphide.

The indole derivatives of formula XVII may be prepared by methods analogous to those described in the accompanying Examples, or by procedures well known from the art.

In a still further procedure, the compounds of formula III above wherein T represents CH, U represents C—$R^2$ and V represents oxygen or sulphur, corresponding to the benzofuran or benzthiophene derivatives of formula IA wherein V is oxygen or sulphur respectively and $R^1$ is hydrogen, may be prepared by a process which comprises cyclising a compound of formula XVIII:

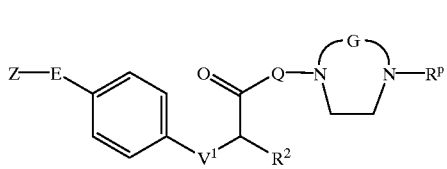
(XVIII)

wherein Z, e, Q, G, $R^2$ and $R^p$ are as defined above, and $V^1$ represents oxygen or sulphur; followed by removal of the amino-protecting group $R^p$.

Similarly, the compounds of formula I wherein T represents CH, U represents C—$R^2$ and V represents oxygen or sulphur—i.e. the benzofuran or benzthiophene derivatives of formula IA above—may be prepared by a process which comprises cyclising a compound of formula XIX:

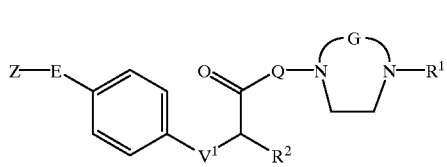
(XIX)

wherein Z, E, Q, G, $R^1$, $R^2$ and $V^1$ are as defined above.

The cyclisation of compounds XVIII and XIX is conveniently effected by using polyphosphoric acid or a polyphosphate ester, advantageously at an elevated temperature.

The compounds of formula XVIII and XIX may be prepared by reacting a compound of formula XX with a compound of formula XXI:

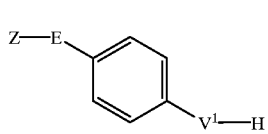
(XX)

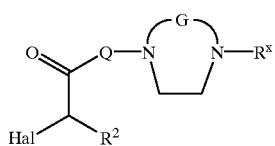
(XXI)

wherein Z, E, Q, G, $R^2$, $V^1$ and $R^x$ are as defined above, and Hal represents a halogen atom.

The reaction is conveniently effected in the presence of a base such as sodium hydroxide.

The hydroxy and mercapto derivatives of formula XX may be prepared by a variety of methods which will be readily apparent to those skilled in the art. One such method is described in EP-A-0497512.

The hydrazine derivatives of formula IV above may be prepared by methods analogous to those described in EP-A-0438230, EP-A-0497512, EP-A-9548813 and WO-A-91/18897, as also may the aniline derivatives of formula XIII.

Where they are not commercially available, the starting materials of formula VII, VIII, XI and XXI may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein $R^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylted under standard conditions, and the mesyl group subsequently displaced by an amino moiety by treatment with the desired amine in a sealed tube at an elevated temperature. The amine derivative resulting from any of these procedures may the, for example, by N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative treatment with the appropriate amine, advantageously in the presence of 1-(3-dimethylaminopropyl)-3-ethylcarbodiimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D_\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D_\alpha}$/5-HT$_{1D_\beta}$ Radioligand Binding

Chinese hamster ovary (CHO) clonal cell lines expressing the human 5-HT$_{1D_\alpha}$ and 5-HT$_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, parglyine 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the 5-HT$_{1D_\alpha}$ receptor subtype obtained for the compounds of the accompanying Examples were below 50 nM in each case. Furthermore, the compounds of the accompanying Examples were all found to possess a selective affinity for the 5-HT$_{1D_\alpha}$ receptor subtype of at least 10-fold relative to the 5-HT$_{1D_\beta}$ subtype.

5-HT$_{1D_\alpha}$/5-HT$_{1D_\beta}$ Adenylyl Cyclase Assay

Studies were performed essentially as described in *J. Pharmacol. Exp. Ther.*, 1986, 238, 248. CHO clonal cell lines expressing the human cloned 5-HT$_{1D_\alpha}$ and 5-HT$_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

5-HT$_{1D_\alpha}$/5-HT$_{1D_\beta}$ GTPγS Binding

Studies were performed essentially as described in *Br. J. Pharmacol.*, 1993, 109, 1120. CHO clonal cell lines expressing the human cloned 5-HT$_{1D_\alpha}$ and 5-HT$_{1D_\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 μg protein/ml for the 5-$HT_{1D_\alpha}$ receptor transfected cells and 40–50 μg protein/ml for the 5-$HT_{1D_\beta}$ receptor transfected cells. The membrane suspension was then incubated, in a volume of 1 ml, with GDP (100 μM for 5-$HT_{1D_\alpha}$ receptor transfected cells, 30 μM for the 5-$HT_{1D_\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D_\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D_\alpha}$ receptor subtype relative to the 5-$HT_{1D_\beta}$ subtype.

EXAMPLE 1

1-Benzyl-4-[3-[5-(1,2,4-triazol-4-yl)-1H-indol-3-yl] propyl]piperazin-2-one. 1.3 Hydrogen Oxalate

Intermediate 1: 4-(tert-Butyloxycarbonyl)piperazin-2-one

A solution of ethyl chloroacetate (20 g, 0.16 mol) in EtOH (50 mL) was added to a stirred solution of ethylenediamine (65 mL, 0.98 mol) in EtOH (300 mL) at 0° C. After addition the cooling bath was removed and the mixture warmed to room temperature. Aft 5 h a solution of sodium methoxide in MeOH (3.7 g Na dissolved in 20 mL MeOH) was added and the mixture stirred for 16 h. The mixture was filtered and the filtrate evaporated in vacuo. The residue as dissolved in EtOH (200 mL) and heated at reflux for 4 h. After this time the solvent was removed by evaporation and the residue partitioned between $CH_2Cl_2$ (200 mL) and water (200 mL). The aqueous layer was separated, dried ($Na_2SO_4$) and evaporated. The residue was dissolved in $CH_2Cl_2$, di-tert-butyldicarbonate (106.6 g, 0.49 mol) was added and the mixture stirred for 1 h. The solution was then washed with water (300 mL) and the organic layer separated, dried ($Na_2SO_4$) and evaporated. The residue was triturated in petrol and the undissolved solid collected by filtration. The solid was chromatographed on silica gel, eluting with $CH_2Cl_2$:MeOH (97:3), to afford 4-(tert-butyloxycarbonyl) piperazin-2-one (10.8 g, 33%) as a colourless solid. mp. 158–161° C. $^1$H NMR (250 MHz, $CDCl_3$) δ 1.48 (9H, s), 3.40 (2H, m), 3.63 (2H, m), 4.10 (2H, s), 6.42 (1H, br s).

Intermediate 2: 3-[5-(1,2,4-Triazol-4-yl)-1H-indol-3-yl]propan-1-ol

A solution of 4-(1,2,4-triazol-4-yl)phenylhydrazine (prepared as described in WO 94/03446, Example 1) (25 g, 143 mmol) in dioxan (250 ml) was treated with dihydropyran (24 g, 286 mmol) followed by 1 M hydrochloric acid (150 ml) and heated at reflux for 18 hours. The reaction mixture was evaporated with toluene then reevaporated. Inorganic solids were removed by treating the residue with a mixture of methanol and acetonitrile. The mother liquors were purified by column chromatography on silica using dichloromethane:methanol (9:1→4:1) as the eluant. The compound was recrystallised from acetonitrile to afford the title compound as a white solid (10.24 g, 30%), mp 205–207° C. δ (360 MHz, $d_6$-DMSO) 1.81 (2H, quintet, J=7Hz, $CH_2$), 2.75 (2H, t, J=8Hz, $CH_2$), 3.46 (2H, dt, $J_1$=6Hz, $J_2$=5Hz, $CH_2$), 4.43 (1H, t, J=5Hz, OH), 7.26 (1H, d, J=2Hz, AR—H), 7.29 (1H, dd, $J_1$=9Hz, $J_2$=2Hz, Ar—H), 7.47 (1H, d, J=9Hz, Ar—H), 7.77 (1H, d, J=2Hz, Ar—H), 9.01 (2H, s, Triazole-H), 11.05 (1H, br s, indole NH). MS, $CI^+$, m/z for $(M+H)^+$=243.

Step 1: 1-Benzyl-4-(tert-butyloxycarbonyl)piperazin-2-one

To a stirred solution solution of Intermediate 1 (1.5 g, 7.5 mmol) in DMF (30 mL) at 0° C., under nitrogen, was added sodium hydride (330 mg of a 60% dispersion in mineral oil. 8.3 mmol). The solution was stirred for 90 min before benzyl bromide (1.16 mL, 9.8 mmol) was added. The solution was heated at 60° C. for 3 h then the solvent was removed in vacuo. The residue was partitioned between EtOAc (2×50 mL) and water (50 mL). The combined organic phases were dried ($Na_2SO_4$) and evaporated. The residue was chromatographed on silica, eluting with petrol:EtOAc (1:1), to afford the title amide (2.11 g, 97%) as a colourless solid. m.p. 85–88° C., $^1$H NMR (250 MHz, $CDCl_3$) δ 1.46 (9H, s), 3.23–3.28 (2H, m), 3.56–3.61 (2H, m), 4.16 (2H, s), 4.63 (2H, s), 7.24–7.35 (5H, m).

Step 2: 1-Benzyl-4-[3-[5-(1,2,4-triazol-4-yl)-1H-indol-3-yl]propyl]piperazin-2-one. 1.3 Hydrogen Oxalate To a stirred solution of 1-benzyl-4-(tert-butyloxycarbonyl)piperazin-2-one (628 mg, 2.2 mmol) in $CH_2Cl_2$ (30 mL) was added trifluoroacetic acid (3 mL) and the solution stirred for 4 h. After this time the solvent was removed in vacuo and the residue azeotroped with toluene (20 mL). The residue was partitioned between EtOAc (2×20 mL) and $K_2CO_3$ (sat., 20 mL). The combined organic phases were dried ($Na_2SO_4$) and evaporated. The resultant piperazinone (262 mg) was isolated as a pale yellow oil and used crude in the subsequent reaction.

To a stirred solution of Intermediate 2 (150 mg, 0.62 mmol) in THF (80 mL) at room temperature was added methanesulphonyl chloride (95 μl, 1.23 mmol) and triethylamine (171 μl, 1.23 mmol). After 3 h more triethylamine (85 μl, 0.62 mmol) followed by methanesulphonyl chloride (47 μl, 0.62 mmol) was added. After stirring for a further 30 min more triethylamine (40 μl, 0.29 mmol) followed by methanesulphonyl chloride (24 μl, 0.29 mmol) was added. The mixture was stirred for a further 30 min whereupon the mixture was filtered and the filtrate removed in vacuo. The crude mesylate was dissolved in iso-propanol (25 mL), and $K_2CO_3$ (297 mg, 1.43 mmol), sodium iodide (93 mg, 0.62 mmol) and the piperazinone (262 mg) prepared from above were added to the solution. The mixture was heated at reflux, in the dark, for 24 h. After cooling to room temperature the mixture was filtered and the filtrate evaporated. The residue was partitioned between $CH_2Cl_2$ (2×30 mL) and water (30 mL). The combined organic layers were dried ($Na_2SO_4$) and evaporated. The residue was chromatographed on silica gel, eluting with CH$_2$Cl$_2$:MeOH (93.7), to afford the title piperazinone (107 mg, 42%) as a colourless oil, as the free base. The hydrogen oxalate salt was prepared. m.p. 129° C. C$_{24}$H$_{26}$N$_6$O. 1.3(C$_2$H$_2$O$_4$) requires: C, 60.11; H, 5.42; N, 15.81%. Found C, 60.31; H, 5.55; N, 15.66%. $^1$H NMR (360 MHz, d$_6$-DMSO) δ 1.83–1.95 (2H, m), 2.59 (2H, t, J=7.2Hz), 2.74 (2H, t, J=7.3Hz), 2.80–2.88 (2H, m), 3.25 (2H, t, J=5.9Hz), 3.29 (2H, s), 4.53 (2H, s), 7.23–7.37 (7H, m), 7.49 (1H, d, J=8.7Hz), 7.79 (1H, d, J=1.9Hz), 9.01 (2H, s), 11.10 (1H, br s). MS (ES$^+$) (415, M+1).

EXAMPLE 2

1-(2-Phenylethyl)-4-(3-[5-(1,2,4-triazol-4-yl)-1H-indol-3-yl]propyl)piperazin-2-one. 1.25 Hydrogen Oxalate Step 1: 2-(Phenylethylamino)ethyl carbamic acid tert-butyl ester A solution of phenylethylamine hydrochloride (2.88 g, 0.018 mol) and 2-bromo-N-tert-butyloxycarbonylethylamine (4.1 g, 0.018 mmol) in DMF (50 mL), containing K$_2$CO$_3$ (5.0 g, 0.036 mol), was heated at 60° C. for 4 h. The solution was filtered, evaporated and the residue partitioned between CH$_2$Cl$_2$ (2×100 mL) and water (100 mL). The combined organic layers were dried (Na$_2$SO$_4$) and evaporated. The residue was chromatographed on silica gel, eluting with CH$_2$Cl$_2$:MeOH (90:10), to afford the title compound (1.44 g, 30%) as a colourless oil. $^1$H NMR (250 MHz, CDCl$_3$) δ 1.44 (9H, s), 2.74 (2H, t, J=6.0Hz), 2.79 (2H, m), 2.88 (2H, m), 3.19 (2H, m), 4.87 (1H, br s), 7.19–7.22 (3H, m), 7.26–7.31 (2H, m). MS (ES$^+$) (265, M+1).

Step 2: 2-[(Bromoacetyl)(2-phenylethyl)amino]ethyl carbamic acid tert-butyl ester To a solution of bromoacetyl bromide (0.25 mL, 2.92 mmol) in CH$_2$Cl$_2$ (10 mL) at −10° C. was added a solution of 2-(phenylethylamino)ethyl carbamic acid tert-butyl ester (0.7 g, 2.65 mmol) and triethylamine (0.41 mL, 2.92 mmol) in CH$_2$Cl$_2$ (10 mL) dropwise. The mixture was stirred at −10° C. for 30 min, before removal of the solvent in vacuo. The residue was partitioned between EtOAc (2×30 mL) and water (30 mL). The combined organic layers were dried (Na$_2$SO$_4$) and evaporated. The residue was chromatographed on silica gel, eluting with petrol:EtOAc (2:1→1:1), to afford the title amide (0.81 g, 79%) as a colourless oil. $^1$H NMR (250 MHz, CDCl$_3$) δ 1.44 (9H, s), 2.86–2.94 (2H, m), 3.10–3.94 (8H, m), 4.59 and 4.92 (1H, 2×br s), 7.15–7.37 (5H, m). MS (ES$^+$) (385/387, M$^+$).

Step 3: 1-(2-Phenylethyl)piperazin-2-one

To a solution of 2-[(bromoacetyl)(2-phenylethyl)amino] ethyl carbamic acid tert-butyl ester (0.81 g, 2.1 mmol) in CH$_2$Cl$_2$ (25 mL) was added trifluoroacetic acid (2.5 mL) and the mixture stirred for 1 h. The solvent was removed in vacuo and the residue azeotroped with toluene (10 mL) and CH$_2$Cl$_2$ (2×10 mL). The crude amine (1.1 g) was isolated as its trifluoroacetate salt, as a pale yellow oil and used crude in the subsequent reaction.

The crude amino trifluoroacetate (1.1 g) was dissolved in EtOH (50 mL), K$_2$CO$_3$ (0.58 g, 4.2 mmol) was added, and the mixture heated at reflux for 20 h. The mixture was cooled to room temperature, filtered and the filtrate evaporated. The residue was partitioned between CH$_2$Cl$_2$ (4×30 mL) and water (30 mL). The combined organic layers were dried (Na$_2$SO$_4$) and evaporated. The residue was chromatographed on silica gel, eluting with CH$_2$Cl$_2$:MeOH:NH$_3$ (90:10:0→90:10:1), to afford the title compound (0.36 g, 84%) as a colourless solid. mp 75–78° C. $^1$H NMR (250 MHz, CDCl$_3$) δ 2.89 (2H, t, J=7.1Hz), 2.97 (2H, m), 3.14 (2H, m), 3.51 (2H, s), 3.59 (2H, t, J=7.2Hz), 7.19–7.33 (5H, m). MS (ES$^+$) (205, M+1).

Step 4: 1-(2-Phenylethyl)-4-(3-[5-(1,2,4-triazol-4-yl)-1H-indol-3-yl]propyl)piperazin-2-one. 1.25 Hydrogen Oxalate To a suspension of Intermediate 2 (150 mg, 0.62 mmol) in THF (80 mL) was added triethylamine (172 μL, 1.23 mmol) and methanesulphonyl chloride (97 μL, 1.23 mmol). The mixture was stirred at room temperature for 90 min before more triethylamine (86 μL, 0.62 mmol) and methanesulphonyl chloride (48 μL, 0.62 mmol) were added. The mixture was stirred for a further 1 h, then filtered and the filtrate evaporated. The crude mesylate was dissolved in iso-propanol (20 mL), and K$_2$CO$_3$ (257 mg, 1.9 mmol), sodium iodide (93 mg, 0.62 mmol) and 1-(2-phenylethyl) piperazin-2-one (348 mg, 1.7 mmol) were added. The mixture was heated at reflux, in the dark, for 20 h. After cooling the mixture was filtered and the filtrate evaporated. The residue was partitioned between CH$_2$Cl$_2$ (2×50 mL) and water (50 mL). The combined organic layers were dried (Na$_2$SO$_4$) and evaporated. The residue was chromatographed on silica gel, eluting with CH$_2$Cl$_2$:MeOH (90:10), to afford the title compound (149 mg, 56%) as the free base as a pale yellow foam. The hydrogen oxalate salt was prepared. mp 97° C. (dec.). C$_{25}$H$_{28}$N$_6$O.1.25(C$_2$H$_2$O$_4$).H$_2$O requires C, 59.08; H, 5.86; N, 15.03%. Found: C, 59.10; H, 5.79; N, 15.15%. $^1$H NMR (360 MHz, d$_6$-DMSO) δ 1.82–1.94 (2H, m), 2.51–2.63 (2H, m), 2.71–2.80 (6H, m), 3.19 (2H, s), 3.22–3.30 (2H, m), 3.48 (2H, t, J=7.4 Hz), 7.19–7.31 (7.48 (1H, d, J=8.6Hz), 7.78 (1H, d, J=1.9 Hz), 9.01 (2H, s), 11.10 (1H, br s). MS (ES$^+$) (429, M+1).

EXAMPLE 3

1-(2-(3-Fluorophenyl)ethyl)-4-(3-[5-(1,2,4-triazol-4-yl)-1H-indol-3-yl]propyl)piperazin-2-one. Hydrogen Oxalate.

Step 1: 2-[(3-Fluorophenyl)acetylamino]ethyl carbamic acid tert-butyl ester

To a solution of 3-fluorophenylacetic acid (1.93 g, 12.5 mmol) in CH$_2$Cl$_2$ (50 mL) was added tert-butyl-N-(2-aminoethyl)carbamate (2.0 g, 12.5 mmol), 4-dimethylaminopyridine (1.53 g, 12.5 mmol) and 1-[3-dimethylamino)propyl]-3-ethyl carbodiimide hydrochloride (2.4 g, 12.5 mmol). The mixture was stirred at room temperature for 16 h then washed with water (50 mL) and citric acid (10%, 2×50 mL). The organic layer was separated, dried (Na$_2$SO$_4$) and evaporated. The residue was chromatographed on silica gel, eluting with CH$_2$Cl$_2$:MeOH (95:5→90:10), to afford the title amide (3.7 g, 100%) as a colourless solid. mp 125–128° C. $^1$H NMR (250 MHz, CDCl$_3$) δ 1.43 (9H, s), 3.18–3.40 (4H, m), 3.53 (2H, s), 4.82 (1H, br s), 6.23 (1H, br s), 6.94–7.06 (3H, m), 7.26–7.40 (2H, m). MS (ES$^+$) (297, M+1).

Step 2: 2-[2-(3-Fluorophenyl)ethylamino]ethyl carbamic acid tert-butyl ester

To a solution of the amide (0.5 g, 1.7 mmol) in THF (25 mL) at 0° C., under nitrogen, was added LiAlH$_4$ (5.1 mL of a 1.0 M solution in ether, 5.1 mmol) dropwise. The cooling bath was removed and the mixture stirred at room temperature for 16 h. After this time more LiAlH$_4$(1.7 mL of a 1.0 M solution in ether, 1.7 mmol) was added dropwise and the mixture stirred for a further 5 h. After this time Na$_2$SO$_4$ (sat., 6.8 mL) was added dropwise at 0° C. and the mixture stirred for a further 15 min. The resultant solid was removed by filtration, the filtrate evaporated, and the residue chromatographed on silica gel, eluting with CH$_2$Cl$_2$:MeOH (90:10). The amine (140 mg, 29%) was isolated as a pale yellow oil. $^1$H NMR (250 MHz, CDCl$_3$) δ 1.44 (9H, s), 2.74–2.95 (6H, m), 3.19–3.25 (2H, m), 4.91 (1H, br s), 6.90–6.99 (3H, m), 7.21–7.30 (2H, m). MS (ES$^+$) (283, M+1).

Step 3: 2-[(Bromoacetyl)(2-[3-fluorophenyl]ethyl) amino]ethyl carbamic acid tert-butyl ester Prepared in the same manner as that described in Example 2, Step 2, using 2-[2-(3-fluorophenyl)ethylamino]ethyl carbamic acid tert-butyl ester (713 mg, 2.53 mmol), bromoacetyl bromide (0.24 mL, 2.78 mmol), triethylamine (0.39 mL, 2.78 mmol) and CH$_2$Cl$_2$ (10 mL). The bromide (855 mg, 84%) was isolated as a yellow oil. $^1$H NMR (360 MHz, CDCl$_3$) δ 1.44 (9H, s), 2.87–2.95 (2H, m), 3.26–3.39 (3H, m), 3.46–3.92 (5H, m), 4.62 and 4.90 (1H, 2×br s), 6.89–7.02 (3H, m), 7.20–7.30 (2H, m). MS (ES$^+$) (403/405, M$^+$).

Step 4: 1-[3-(3-Fluorophenyl)ethyl]piperazin-2-one

Prepared in the same manner as that described in Example 2, Step 3 using 2-[(bromoacetyl)(2-[3-fluorophenyl]ethyl)amino]ethyl carbamic acid tert-butyl ester (0.85 g, 2.1 mmol), trifluoroacetic acid (2.5 mL) and CH$_2$Cl$_2$ (25 mL), followed by K$_2$CO$_3$ (0.58 g, 4.2 mmol) and EtOH (50 mL). The piperazinone (351 mg, 75%) was isolated as a pale yellow oil. $^1$H NMR (250 MHz, CDCl$_3$) δ290 (2H, t, J=7.1Hz), 2.97–3.01 (2H, m), 3.14–3.18 (2H, m), 3.52 (2H, s), 3.58 (2H, t, J=7.2Hz), 6.89–7.03 (3H, m), 7.22–7.31 (2H, m). MS (ES$^+$) (223, M+1).

Step 5: 1-(2-(3-Fluorophenyl)ethyl)-4-(3-[5-(1,2,4-triazol-4-yl)-1H-indol-3-yl]propyl)piperazin-2one. Hydrogen Oxalate In the same manner as that described in Example 2, Step 4, using Intermediate 2 (150 mg, 0.62 mmol), triethylamine (1.72 μL, 1.24 mmol), methanesulphonyl chloride (96 μl, 1.24 mmol) and THF (80 mL), followed by more triethylamine (86 μl, 0.62 mmol) and methanesulphonyl chloride (48 μl, 0.62 mmol). The resultant crude mesylate was then treated with 1-[2-(3-fluorophenyl)ethyl]piperazin-2-one (341 mg, 1.55 mmol), K$_2$CO$_3$ (257 mg, 1.9 mmol), sodium iodide (93 mg, 0.62 mmol) and iso-propanol (25 mL). The title compound (159 mg, 58%) was isolated as the free base as a colourless foam. The hydrogen oxalate salt was prepared. mp 88° C. (dec.). C$_{25}$H$_{27}$N$_6$OF. C$_2$H$_2$O$_4$. H$_2$O requires: C, 58.48; H, 5.63; N, 15.15%. Found: C, 58.58; H, 5.77; N, 15.01%. $^1$H NMR (360 MHz, d$_6$-DMSO) δ 1.84–1.96 (2H, m), 2.55 (2H, t, J=7.6Hz), 2.74 (2H, t, J=7.3Hz), 2.78–2.82 (4H, m), 3.19 (2H, s), 3.24–3.28 (2H, m), 3.51 (2H, t, J=7.9Hz), 7.00–7.09 (3H, m), 7.29–7.36 (3H, m), 7.48 (1H, d, J=8.6Hz), 7.79 (1H, d, J=1.9Hz), 9.01 (2H, s), 11.10 (1H, br s). MS (ES$^+$) (447, M+1).

EXAMPLE 4

1-[2-(3,4-Difluorophenyl)ethyl]-4-(3-[5-(1,2,4-triazol-4yl)-1H-indol-3-yl]propyl)piperazin-2-one. 1.3 Hydrogen Oxalate Step 1: 2-[2-(3,4-Difluorophenyl)ethylamino]ethyl carbamic acid tert-butyl ester To a solution of tert-butyl-N-(2-aminoethyl)carbamate (718 mg, 4.5 mmol) in MeOH (40 mL) at 0° C., under nitrogen, was added (3,4-difluorophenyl)acetaldehyde (0.7 g, 4.5 mmol) in MeOH (10 mL), acetic acid (0.78 mL, 13.5 mmol) and sodium cyanoborohydride (564 mg, 9.0 mmol). After stirring at 0° C. for 15 min the cooling bath was removed and the mixture stirred at room temperature for 3 h. Saturated K$_2$CO$_3$ solution (50 mL) was added and the mixture stirred for a further 15 min. The solvents were removed in vacuo and the residue partitioned between water (50 mL) and EtOAc (2×50 mL). The combined organic layers were dried (Na$_2$SO$_4$), and evaporated. The residue was chromatographed on silica gel, eluting with CH$_2$Cl$_2$:MeOH:NH$_3$ (90:10:1) to give the amine (473 mg, 35%) as a yellow oil. $^1$H NMR (250 MHz, CDCl$_3$) δ 1.44 (9H, s), 2.72–2.78 (4H, m), 2.83–2.90 (2H, m), 3.18–3.28 (2H, m), 4.87 (1H, br s), 6.87–7.13 (3H, m). MS (ES$^+$) (301, M+1).

Step 2: 2-[(Bromoacetyl)(2-(3,4-difluorophenyl) ethyl)amino]ethyl carbamic acid tert-butyl ester Prepared in the same manner as that described in Example 2, Step 2 using 2-[2-(3,4-difluorophenyl)ethylamino]ethyl carbamic acid tert-butyl ester (473 mg, 1.6 mmol), bromoacetyl bromide (0.15 mL, 1.7 mmol), triethylamine (0.24 mL, 1.7 mmol) and CH$_2$Cl$_2$ (10 mL). The bromide (549 mg, 83%) was isolated as a yellow oil. $^1$H NMR (250 MHz, CDCl$_3$) δ 1.43 (9H, s), 2.81–2.93 (2H, m), 3.17–3.40 (3H, m), 3.46–3.95 (5H, m), 4.66 and 4.90 (1H, 2×br s), 6.93–7.19 (3H, m). MS (ES$^+$) (421/423, M$^+$).

Step 3: 1-[2-(3,4-Difluorophenyl)ethyl]piperazin-2-one

In the same way as that described in Example 2, Step 3 using 2-[(bromoacetyl)(2-(3,4-difluorophenyl)ethyl)amino] ethyl carbamic acid tert-butyl ester (549 mg, 1.3 mmol), trifluoroacetic acid (2.5 mL) and CH$_2$Cl$_2$ (25 mL), followed by K$_2$CO$_3$ (0.36 g, 2.6 mmol) and EtOH (50 mL). The piperazinone (286 mg, 91%) was isolated as a yellow oil. $^1$H NMR (250 MHz, CDCl$_3$) δ 2.85 (2H, t, J=7.3Hz), 2.99–3.03 (2H, m), 3.17–3.21 (2H, m), 3.52 (2H, s), 3.56 (2H, t, J=7.3Hz), 6.90–7.16 (3H, m). MS (ES$^+$) (241, M+1).

Step 4: 1-[2-(3,4-Difluorophenyl)ethyl]-4-(3-[5-(1,2, 4-triazol-4-yl)-1H-indol-3-yl]propyl)piperazin-2-one. 1.3 Hydrogen Oxalate In the same manner as that described in Example 2, Step 4, using Intermediate 2 (150 mg, 0.62 mmol), triethylamine (172 μL, 1.24 mmol), methanesulphonyl chloride (96 μL, 1.24 mmol) and THF (80 mL), followed by more triethylamine (86 μL, 0.62 mmol) and methanesulphonyl chloride (48 μL, 0.62 mmol). The resultant crude mesylate was then treated with 1-[2-(3,4-difluorophenyl)ethyl]piperazin-2-one (258 mg, 1.2 mmol), K$_2$CO$_3$ (257 mg, 1.9 mmol), sodium iodide (9.3 mg, 0.62 mmol) and iso-propanol (20 mL). The crude product was chromatographed on silica gel, eluting with CH$_2$Cl$_2$:MeOH (93:7), to afford the title compound (113 mg, 39%) as a yellow foam. The hydrogen oxalate salt was prepared. mp. 102° C. (dec.). C$_{25}$H$_{26}$N$_6$OF$_2$. 1.3 (C$_2$H$_2$O$_4$). 0.5 (H$_2$O) requires: C, 56.13; H, 5.05; N, 14.23%. Found: C, 56.19; H, 5.02; N, 14.30%. $^1$H NMR (360 MHz, d$_6$-DMSO) δ 1.82–1.95 (2H, m), 2.50–2.59 (2H, m), 2.68–2.83 (6H, m), 3.15 (2H, s), 3.23–3.29 (2H, m), 3.49 (2H, t, J=7.9Hz), 7.05–7.10 (1H, m), 7.28–7.34 (4H, m), 7.48 (1H, d, J=8.6Hz), 7.78 (1H, s), 9.01 (2H, s), 11.09 (1H, br s). MS (ES$^+$) (465, M+1).

EXAMPLE 5

1-Benzyl-4-[3-[5-(1,2,4-triazol-4-yl)-1H-indol-3-yl] propyl]piperazin-2-thione

Step 1: 1-Benzyl-4-(tert-butyloxycarbonyl) piperazin-2-thione

A mixture of 1-benzyl-4-(tert-butyloxycarbonyl) piperazin-2-one (1.0 mg, 3.4 mmol) and 2,4-bis(4- methoxyphenyl)-1,3-dithia-2,4-diphosphetane-2,4-disulphide (Lawesson's Reagent) (837 mg, 2.1 mmol) were heated at 90° C. in toluene (10 mL), under nitrogen for 45 min. The mixture was cooled then partitioned between EtOAc (3×50 mL) and water (50 mL). The combined organic layers were dried ($Na_2SO_4$) and evaporated. The residue was chromatographed on silica gel, eluting with $CH_2Cl_2$:EtOAc (100:0→95:5→90:10) to afford the title compound (853 mg, 82%) as a colourless solid. mp. 126–129° C. $^1$H NMR (250 MHz, $CDCl_3$) δ 1.47 (9H, s), 3.40–3.44 (2H, m), 3.60–3.65 (2H, m), 4.67 (2H, s), 5.31 (2H, s), 7.31–7.39 (5H, m). MS (ES$^+$) (307, M+1).

Step 2: 1-Benzylpiperazin-2-thione

To a solution of 1-benzyl-4-(tert-butyloxycarbonyl) piperazin-2-thione (925 mg, 3.02 mmol) in $CH_2Cl_2$ (25 mL) was added trifluoroacetic acid (2.5 mL). The mixture was stirred at room temperature, under nitrogen, for 2 h. The solvent was evaporated and the residue azeotroped with toluene (2×10 mL). The residue was partitioned between $CH_2Cl_2$ (2×50 mL) and $Na_2CO_3$ solution (10% (w/v), 40 mL). The combined organic layers were dried $Na_2SO_4$) and evaporated. The residue was chromatographed on silica, eluting with $CH_2Cl_2$:MeOH (95:5) to afford the title compound (539 mg, 87%) as a pale orange solid. mp. 70–73° C. $^1$H NMR (250 MHz, $CDCl_3$) δ3.11–3.16 (2H, m), 3.29–3.33 (2H, m), 4.10 (2H, s), 5.31 (2H, s), 7.30–7.37 (5H, m). MS (ES$^+$) (207, M+1).

Step 3: 1-Benzyl-4-[3-[5-(1,2,4-triazol-4-yl)-1H-indol-3-yl)propyl]piperazin-2-thione In the same way as that described in Example 2, Step 4, using Intermediate 2 (150 mg, 0.62 mmol), methanesulphonyl chloride (96 μL, 1.24 mmol), triethylamine (172 μL, 1.24 mmol) and THF (80 mL), followed by more triethylamine (86 μL, 0.62 mmol) and methanesulphonyl chloride (48 μL, 0.62 mmol). The resultant crude mesylate was then treated with 1-benzylpiperazine-2-thione (255 mg, 1.24 mmol), $K_2CO_3$ (257 mg, 1.9 mmol), sodium iodide (93 mg, 0.62 mmol) and iso-propanol (20 mL). The crude produce was chromatographed on silica gel, eluting with $CH_2Cl_2$:MeOH:$NH_3$ (95:5:1), to give the title compound (104 mg) as a pale yellow foam, contaminated with some 1-benzylpiperazin-2-thione. The mixture of thioamides (104 mg) was dissolved in $CH_2Cl_2$ (25 mL) and treated with di-tert-butyldicarbonate (50 mg, 0.23 mmol). The mixture was stirred at room temperature for 2 h then the solvent removed in vacuo. The residue was chromatographed on silica gel, eluting with $CH_2Cl_2$:MeOH (95:5), to afford the title compound (47 mg, 18%) as a colourless solid, mp. (MeOH) 201–203° C. $C_{24}H_{26}N_6S$. 0.3($H_2O$) requires: C, 66.12; H, 6.15; N, 19.28%. Found: C, 66.09; H, 5.92; N, 19.23%. $^1$H NMR (360 MHz, d$_6$-DMSO) δ1.81–1.92 (2H, m), 2.42 (2H, t, J=7.1 Hz), 2.70–2.76 (4H, m), 3.37–3.42 (2H, m), 3.61 (2H, s), 7.27–7.38 (7H, m), 7.47 (1H, d, J=8.6 Hz), 7.77 (1H, s), 9.01 (2H, s), 11.07 (1H, br s). MS (ES$^+$) (431, M+1).

EXAMPLE 6

1-(2-Phenylpropyl)-4-(3-[5-(1,2,4-triazol-4-yl)-1H-indol-3-yl]propyl)piperazin-2-one. 1.4 Hydrogen Oxalate Step 1: 2-[2-Phenylpropylamino]ethyl carbamic acid tert-butyl ester In the same way as that described in Example 4, Step 1, using tert-butyl-N-(2-aminoethyl)carbamate (1.6 g, 10 mmol), 2-phenylpropionaldehyde (1.32 mL, 10 mmol), MeOH (100 mL), acetic acid (1.72 mL, 30 mmol) and sodium cyanoborohydride (1.26 g, 20 mmol). The crude residue was chromatographed on silica gel, eluting with $CH_2Cl_2$:MeOH (90:10), to give the amine (1.56 g, 56%) as a colourless oil. $^1$H NMR (250 MHz, $CDCl_3$) δ1.26 (3H, d, J=6.9 Hz), 1.42 (9H, s), 2.70–2.81 (4H, m), 2.90–3.00 (1H, m), 3.14–3.24 (2H, m), 4.89 (1H, br s), 7.19–7.35 (5H, m).

Step 2: 2-[(Bromoacetyl)(2-phenylpropyl)amino] ethyl carbamic acid tert-butyl ester Prepared in the same manner as that described in Example 2, Step 2 using 2-]2-phenylpropylamino]ethyl carbamic acid tert-butyl ester (1.56 g, 5.6 mmol), bromoacetyl bromide (0.52 mL, 5.96 mmol), triethylamine (0.83 mL, 5.96 mmol) and $CH_2Cl_2$ (60 mL). The bromide (1.64 g, 73%) was isolated as a colourless oil. $^1$H NMR (250 MHz, $CDCl_3$) δ1.28 and 1.35 (3H, 2 x d, J=6.9 Hz each), 1.42 and 1.43 (9H, 2 x s), 2.84–3.98 (9H, m), 4.50 and 4.87 (1H, 2 x br s), 7.15–7.36 (5H, m).

Step 3: 1-(2-Phenylpropyl)piperazin-2-one

In the same way as that described in Example 2, Step 3, using 2-[(bromoacetyl)(2-phenylpropyl)amino]ethyl carbamic acid tert-butyl ester (1.64 g, 4.11 mmol), trifluoroacetic acid (4 mL) and $CH_2Cl_2$ (40 mL), followed by $K_2CO_3$ (1.1 g, 8.2 mmol) and EtOH (100 mL). The piperazinone (668 mg, 75%) was isolated as a colourless oil. $^1$H NMR (250 MHz, $CDCl_3$) δ1.28 (3H, d, J=6.8 Hz), 2.72–2.93 (3H, m), 3.04–3.26 (3H, m), 3.28 (1H, d, J=17.3 Hz), 3.52 (1H, d, J=17.3 Hz), 3.85–3.93 (1H, m), 7.19–7.35 (5H, m).

Step 4: 1-(2-Phenylpropyl)-4-(3-[5-(1,2,4-triazol-4-yl)-1H-indol-3-yl]propyl)piperazin-2-one. 1.4 Hydrogen Oxalate In the same manner as that described in Example 2, Step 4, using Intermediate 2 (150 mg, 0.62 mmol), triethylamine (172 μL, 1.24 mmol), methanesulphonyl chloride (96 μL, 1.24 mmol) and THF (75 mL), followed by more triethylamine (172 μL, 1.24 mmol) and methanesulphonyl chloride (96 μL, 1.24 mmol). The resultant crude mesylate was then treated with 1-(2-phenylpropyl)piperazin-2-one (332 mg, 1.52 mmol), $K_2CO_3$ (197 mg, 1.42 mmol), sodium iodide (93 mg, 0.62 mmol) and iso-propanol (25 mL). The crude product was chromatographed on silica gel, eluting with $CH_2Cl_2$:MeOH (90:10), to afford the title compound (94 mg, 34%) as a colourless foam. The hydrogen oxalate salt was prepared. mp. 140° C. $C_{26}H_{30}N_6O$. 1.4($C_2H_2O_4$). 0.3 ($H_2O$) requires: C, 60.26; H, 5.87; N, 14.64%. Found: C, 60.57; H, 6.26; N, 14.65%. $^1$H NMR (360 MHz, d$_6$-DMSO) δ1.16 (3H, d, J=6.9 Hz), 1.80–1.92 (2H, m), 2.69–2.73 (4H, m), 3.00–3.06 (1H, m), 3.07–3.30 (6H, m), 3.61 (2H, m), 7.17–7.31 (7H, m), 7.47 (1H, d, J=8.5 Hz), 7.76 (1H, d, J=2.0 Hz), 9.01 (2H, s), 11.09 (1H, br s). MS (ES$^+$) (443, M+1).

EXAMPLE 7

1-(1-Phenylethyl)-4-(3-[5-(1,2,4-triazol-4-yl)-1H-indol-3-yl]propyl)piperazin-2-one. Hydrogen Oxalate Step 1: 1-(1-Phenylethyl)-4-(tert-butyloxycarbonyl) piperazin-2-one In the same way as that described in Example 1, Step 1, using Intermediate 1 (500 mg, 2.5 mmol), sodium hydride (110 mg of a 60% dispersion in mineral oil, 2.8 mmol), (1-bromoethyl)benzene (0.44 mL, 3.25 mmol) and DMF (12 mL). The title piperazinone (677 mg, 89%) was isolated as a colourless oil, which solidified on standing at 0° C. mp. 62–64° C. $^1$H NMR (250 MHz, CDCl$_3$) δ1.40 (9H, s), 1.53 (3H, d, J=7.2 Hz), 2.80–2.90 (1H, m), 3.14–3.36 (2H, m), 3.56–3.71 (1H, m), 4.07 (1H, d, J=18.2 Hz), 4.22 (1H, d, 18.2 Hz), 6.08 (1H, q, J=7.2 Hz), 7.28–7.39 (5H, m).

Step 2: 1-(1-Phenylethyl)piperazin-2-one

Prepared in the same manner as that described in Example 5, Step 2, using 1-(1-phenylethyl)-4-(tert-butyloxycarbonyl) piperazin-2-one (673 mg, 2.2 mmol), trifluoroacetic acid (4 mL) and CH$_2$Cl$_2$ (40 mL). The crude product was chromatographed on silica gel, eluting with CH$_2$Cl$_2$:MeOH (90:10), to afford the amine (307 mg, 68%) as a colourless oil. $^1$H NMR (250 MHz, CDCl$_3$) δ1.53 (3H, d, J=7.2 Hz), 2.75–2.94 (2H, m), 2.98–3.07 (1H, m), 3.12–3.21 (1H, m), 3.62 (2H, s), 6.13 (1H, q, J=7.2 Hz), 7.24–7.39 (5H, m).

Step 3: 1-(1-Phenylethyl)-4-(3-[5-(1,2,4-triazol-4-yl)-1H-indol-3-yl]propyl)piperazin-2-one. Hydrogen Oxalate In the same was as that described in Example 5, Step 3, using Intermediate 2 (150 mg, 0.62 mmol), triethylamine (172 μL, 1.24 mmol), methanasulphonyl chloride (96 μL, 1.24 mmol) and THF (75 mL), followed by more triethylamine (172 μL, 1.24 mmol) and methanesulphonyl chloride (96 μL, 1.24 mmol). The resultant crude mesylate was then treated with 1-(1-phenylethyl)piperazin-2-one (302 mg, 1.48 mmol), K$_2$CO$_3$ (197 mg, 1.42 mmol), sodium iodide (93 mg, (93 mg, 0.62 mmol) and iso-propanol (25 mL). The crude product was chromatographed on silica gel, eluting with CH$_2$Cl$_2$:MeOH (93:7), to afford the title compound (77 mg), as a colourless oil, contaminated with a small amount of 1-(1-phenylethyl)piperazin-2-one. This mixture was then dissolved in CH$_2$Cl$_2$ (10 mL) and treated with di-tert-butyldicarbonate (8 mg, 0.04 mmol). The mixture was stirred at room temperature for 2 h, then the solvent removed in vacuo. The residue was chromatographed on silica gel, eluting with CH$_2$Cl$_2$:MeOH (93:7), to give the title piperazinone (50 mg, 19%) as a colourless oil. The hydrogen oxalate salt was prepared. mp. 140° C. (dec.). C$_{25}$H$_{28}$N$_6$O. C$_2$H$_2$O$_4$. H$_2$O requires: C,60.44; H, 6.01; N, 15.66%. Found C, 60.44; H, 5.94; N, 15.58%. $^1$H NMR (360 MHz, d$_6$-DMSO) δ1.45 (3H, d, J=7.2 Hz), 1.82–1.95 (2H, m), 2.54–2.62 (2H, m), 2.63–2.90 (6H, m), 3.22–3.38 (3H, m), 5.80 (1H, q, J=7.2 Hz), 7.26–7.38 (7H, m), 7.48 (1H, d, J=8.5 Hz), 7.78 (1H, d, J=1.9 Hz), 9.00 (2H, s), 11.09 (1H, br s). MS (ES$^+$) (429, M+1).

EXAMPLE 8

1-(2-Phenylpropyl)-4-(3-[5-(1,2,4-triazol-4-yl)-1H-indol-3-yl]propyl)piperazin-3-one. Hydrogen Oxalate Step 1: 2-[(3-[5-(1,2,4-Triazol-4-yl)-1H-indol-3-yl]propyl)amino]ethyl carbamic acid tert-butyl ester To a suspension of Intermediate 2 (0.8 g, 3.3 mmol) in THF (250 ml) was added triethylamine (0.51 ml, 6.6 mmol) and methanesulphonyl chloride (0.92 ml, 6.6 mmol). The mixture was stirred at room temperature for 90 min. After this time the mixture was filtered and the filtrate evaporated. The crude mesylate was used directly without further purification.

The crude mesylate was dissolved in iso-propanol (130 ml) and K$_2$CO$_3$ (1.37 g, 9.9 mmol), sodium iodide (496 mg, 3.3 mmol) and tert-butyl-N-(2-aminoethyl)carbamate (1.32 g, 8.3 mmol) were added. The mixture was heated at reflux, in the dark, for 9 h. after cooling the mixture was filtered and the filtrate evaporated. The residue was partitioned between water (100 ml) and CH$_2$Cl$_2$ (2×100 ml). The combined organic layers were dried (Na$_2$SO$_4$) and evaporated. The residue was chromatographed on silica gel, eluting with CH$_2$Cl$_2$:MeOH:NH$_3$ (90:10:1), to afford the title compound (0.42 g, 33%) as a pale yellow foam. $^1$H NMR (250 MHz, CDCl$_3$) δ1.44 (9H, s), 1.84–1.96 (2H, m), 2.68–2.85 (6H, m), 3.16–3.26 (2H, m), 4.91 (1H, br s), 7.13–7.17 (2H, m), 7.48 (1H, d, J=8.6 Hz), 7.56 (1H, d, J=2.1 Hz), 8.48 (2H, s), 8.53 (1H, br s). MS (ES$^+$) (385, M+1).

Step 2: 2-[(Phenylmethyl)(3-[5-(1,2,4-triazol-4-yl)-1H-indol-3-yl]propyl)amino]ethyl carbamic acid tert-butyl ester To a solution of 2-[(3-[5-(1,2,4-triazol-4-yl)-1H-indol-3-yl]propyl)amino]ethyl carbamic acid tert-butyl ester (0.42 g, 1.2 mmol) in methanol (10 ml) at 0° C. was added benzaldehyde (133 μl, 1.3 mmol), acetic acid (189 μl, 3.3 mmol) and sodium cyanoborohydride (137 mg, 2.2 mmol). After addition the cooling bath was removed and the mixture stirred for 4 h. After this time more benzaldehyde (110 μl, 1.1 mmol) was added and the mixture stirred for 18 h. More benzaldehyde (110 μl, 1.1 mmol) was added and the mixture stirred for a further 10 min. The solvents were evaporated and the residue partitioned between EtOAc (2×50 ml) and water (50 ml). The combined organic layers were dried (Na$_2$SO$_4$) and evaporated. The residue was chromatographed on silica gel, eluting with CH$_2$Cl$_2$:MeOH:NH$_3$ (95:5:1), to give the desired product (0.44 g, 85%) as a pale yellow foam. $^1$H NMR (360 MHz, CDCl$_3$) δ1.41 (9H, s), 1.84–1.96 (2H, m), 2.52–2.58 (4H, m), 2.75 (2H, t, J=7.5 Hz), 3.12–3.20 (2H, m), 3.58 (2H, s), 4.78 (1H, br s), 7.03 (1H, s), 7.14 (1H, dd, J=8.5 and 2.0 Hz), 7.21–7.36 (5H, m), 7.45 (1H, d, J=8.5 Hz), 7.51 (1H, d, J=2.0 Hz), 8.29 (1H, br s), 8.45 (2H, s). MS (ES$^+$) (475, M+1).

Step 3: N-(Phenylmethyl)-N-(3-[5-(1,2,4-triazol-4-yl)-1H-indol-3-yl]propyl)ethylenediamine A solution of 2-[(phenylmethyl)(3-[5-(1,2,4-triazol-4-yl)-1H-indol-3-yl]propyl)amino]ethyl carbamic acid tert-butyl ester (440 mg, 0.93 mmol) and trifluoroacetic acid (3 ml) in CH$_2$Cl$_2$ (20 ml) was stirred at room temperature for 5 h. After this time the solvent was evaporated and the residue azeotroped with CH$_2$Cl$_2$ (20 ml) and toluene (20 ml). The residue was partitioned between CH$_2$Cl$_2$ (2×30 ml) and K$_2$CO$_3$ (10%; 20 ml). the combined organic layers were dried (NaSO$_4$) and evaporated. The amine (287 mg, 83%, which was isolated as a colourless foam was used without further purification. $^1$H NMR (250 MHz, CDCl$_3$+d$_4$-MeOH) δ1.83–1.99 (2H, m), 2.44–2.59 (4H, m), 2.61–2.79 (4H, m) 3.58 (2H, s), 7.07 (1H, s), 7.11 (1H, dd, J=8.6 and 2.1 Hz), 7.20–7.32 (5H, m), 7.48 (1H, d, J=8.6 Hz), 7.51 (1H, d, J=2.1 Hz), 8.49 (2H, s).

Step 4: Ethyl 2-[(phenylmethyl)(3-[5-(1,2,4-triazol-4-yl)-1H-indol-3-yl]propyl)amino]ethylamino acetate To a solution of N-(phenylmethyl)-N-(3-[5-(1,2,4-triazol-4-yl)-1H-indol-3-yl]propyl)ethylenediamine (125 mg, 0.33 mmol) in DMF (10 ml) containing K$_2$CO$_3$ (46 mg, 0.33 mmol), was added ethyl bromoacetate (37 μl, 0.33 mmol) at 0° C. The mixture was stirred at 0° C. for 4 h then the solvent was evaporated and the residue partitioned between CH$_2$Cl$_2$ (2×20 ml) and water (20 ml). The combined organic layers were dried (NaSO$_4$) and evaporated. The residue was chromatographed on silica gel, eluting with CH$_2$Cl$_2$:MeOH (90:10), to give the ester (94 mg, 62%) as a colourless oil. $^1$H NMR (250 MHz, CDCl$_3$) δ1.23 (3H, t, J=7.2 Hz), 1.84–1.99 (2H, m), 2.52–2.80 (6H, m), 3.31 (2H, s), 3.60 (2H, s), 4.15 (2H, q, J=7.2 Hz), 7.01 (1H, s), 7.14 (1H, dd, J=8.5 and 2.1 Hz), 7.21–7.30 (5H, m), 7.45 (1H, d, J=8.5 Hz), 7.58 (1H, d, J=2.1 Hz), 8.35 (1H, br s), 8.48 (2H, s). MS (ES$^+$) (461, M+1).

Step 5: 1H-4-(3-[5-(1,2,4-triazol-4-yl)-1H-indol-3-yl]propyl)piperazin-3-one

A solution of ethyl 2-[(phenylmethyl)(3-[5-(1,2,4-triazol-4-yl)-1H-indol-3-yl]propyl)amino]ethylamino acetate (94 mg, 0.25 mmol) in EtOH (20 ml) containing 1M HCl (2 ml) and palladium on carbon (121 mg (10% Pd)) was hydrogenated at 40 psi for 3 h. After this time the catalyst was removed by filtration. The filtrate was evaporated and the residue azeotroped with ethanol (20 ml). The amine hydrochloride was isolated as a colourless foam and used directly in the subsequent reaction.

The amine hydrochloride prepared above was dissolved in EtOH (8 ml) and heated at reflux for 2 h in the presence of K$_2$CO$_3$ (56 mg, 0.41 mmol). The solvent was then evaporated and the residue partitioned between CH$_2$Cl$_2$ (20 ml) and water (20 ml). The aqueous layer was then extracted with BuOH (3×15 ml) and the combined BuOH layers evaporated. The residue was chromatographed on silica gel, eluting with CH$_2$Cl$_2$:MeOH:NH$_3$ (60:8:1), to afford the title piperazinone (42 mg, 40%) as a colourless oil $^1$H NMR (250 MHz, CDCl$_3$) δ1.94–2.07 (2H, m), 2.80 (2H, t, J=7.2 Hz), 3.02 (2H, t, J=5.7 Hz), 3.31–3.37 (2H, m), 3.41–3.45 (4H, m), 7.13 (1H, dd, J=8.6 and 2.1 Hz), 7.23 (1H, s), 7.49 (1H, d, J=8.6 Hz), 7.58 (1H, d, J=2.1 Hz), 8.60 (2H, s). MS (ES$^+$) (325, M+1).

Step 6: 1-(2-Phenylpropyl)-4-(3-[5-(1,2,4-triazol-4-yl)-1H-indol-3-yl]propyl)piperazin-3-one. Hydrogen Oxalate To a stirred solution of 1H-4-(3-[5-(1,2,4-triazol-4-yl)-1H-indol-3-yl]propyl)piperazin-3-one (42 mg, 0.13 mmol) in MeOH (7 ml) containing acetic acid (22 μl, 0.39 mmol) was added 2-phenylpropionaldehyde (17 μl, 0.13 mmol) followed by sodium cyanoborohydride (16 mg, 0.26 mmol). After stirring for 2 h K$_2$CO$_3$ (sat., 4 ml) was added and the mixture stirred for 10 min. The solvent was then evaporated and the residue partitioned between CH$_2$Cl$_2$ (2×20 ml) and water (20 ml). The combined orgainic layers were dried (Na$_2$SO$_4$) and evaporated. The residue was chromatographed on silica gel, eluting with CH$_2$Cl$_2$ (90:10), to give the title compound (49 mg, 86%) as a colourless oil. The hydrogen oxalate salt was prepared m.p. 135° C. C$_{26}$H$_{30}$N$_6$O. 1.3(C$_2$H$_2$O$_4$). 0.5(H$_2$O) requires: C, 60.41; H, 5.96; N, 14.78%. Found: C, 60.15; H, 6.13; N, 14.70%. $^1$H NMR (360 MHz, d$_6$-DMSO) δ1.18 (3H, d, J=6.9 Hz), 1.82–1.92 (2H, m), 2.60 (2H, d, J=7.4 Hz), 2.68 (2H, t, J=7.6 Hz), 2.70–2.80 (2H, m), 2.86–3.05 (1H, m), 3.10 (2H, s), 3.26–3.30 (2H, m), 3.33–3.38 (2H, m), 7.16–7.32 (7H, m), 7.48 (1H, d, J=8.5 Hz), 7.77 (1H, d, J=2.0 Hz), 9.02 (2H, s), 11.09 (1H, br s). MS (ES$^+$) (443, M+1).

What is claimed is:

1. A compound of formula I, or a salt thereof:

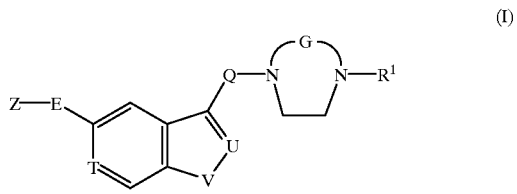

wherein

Z represents —SO$_2$NR$^5$R$^6$ or a group of formula:

(Zb)

in which the asterisk * denotes a chiral centre; or

Z represents an optionally substituted 1,2,4-triazol-1-yl or 1,2,4-triazol-4-yl moiety, the optional substituents being one or more groups selected from methyl, ethyl, benzyl, and amino;

X represents oxygen;

Y$^1$ represents oxygen;

E represents a chemical bond or a straight or branched C$_{1-4}$ alkylene chain;

Q represents a straight or branched C$_{1-6}$ alkylene chain, optionally substituted in any position by one or more substituents selected from fluoro and hydroxy;

T represents CH;

U represents C—R$^2$;

V represents N—R$^3$;

G represents a group of formula (Ga) or (Gc):

(Ga)
—CH$_2$—C(=Y$^2$)—

(Gc)
—C(=Y$^2$)—CH$_2$— in which

Y$^2$ represents oxygen or sulphur;

R$^1$ represents benzyl, 1-phenylethyl, 2-phenylethyl, fluoro-phenylethyl, difluoro-phenylethyl, or 2-phenylpropyl;

R$^2$, R$^3$ and R$^4$ independently represent hydrogen or C$_{1-6}$ alkyl; and

R$^5$ and R$^6$ independently represent hydrogen or methyl.

2. A compound as claimed in claim 1 wherein Q represents a straight or branched C$_{1-6}$ alkylene chain, optionally substituted in any position by a hydroxy group; and R$^5$ and R$^6$ independently represent hydrogen or methyl.

3. A compound as claimed in claim 2 represented by formula IIA, and salts thereof:

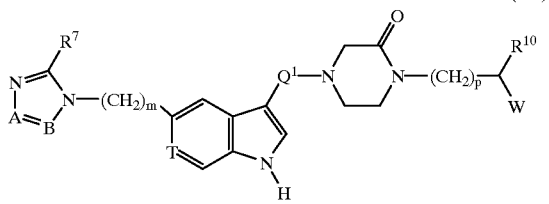

(IIA)

wherein m is zero, 1, 2 or 3;

p is zero or 1;

$Q^1$ represents a straight or branched $C_{2-5}$ alkylene chain, optionally substituted in any position by a hydroxy group;

T represents CH;

A represents nitrogen or CH;

B represents nitrogen or C—$R^8$, with the provisos that both A and B cannot simultaneously represent nitrogen and that when A represents CH, B cannot represent C—$R^8$;

$R^7$ and $R^8$ independently represent hydrogen, methyl, ethyl, benzyl, or amino;

W represents a group of formula (Wa);

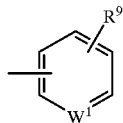

(Wa)

in which $W^1$ represents CH;

$R^9$ represents hydrogen or fluoro; and $R^{10}$ represents hydrogen or methyl, with the proviso that $R^9$ cannot represent fluoro when p is zero an $R^{10}$ represents hydrogen or when p is 1 and $R^{10}$ represents methyl.

4. The compound according to claim 1 of formula IIB, and salts thereof:

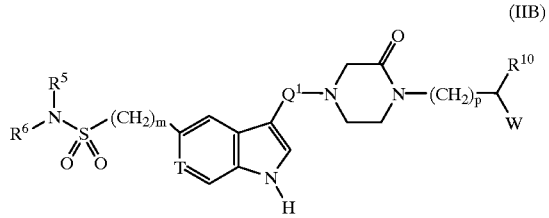

(IIB)

wherein m is zero, 1, 2 or 3;

p is zero or 1;

$Q^1$ represents a straight or branched $C_{2-5}$ alkylene chain optionally substituted in any position by a hydroxy group;

W represents a group of formula (Wa);

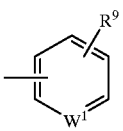

(Wa)

in which $W^1$ represents CH;

$R^9$ represents hydrogen or fluoro; and $R^{10}$ represents hydrogen or methyl, with the proviso that $R^9$ cannot represent fluoro when p is zero and $R^{10}$ represents hydrogen or when p is 1 and $R^{10}$ represents methyl;

and $R^5$ and $R^6$ are as defined in claim 1.

5. The compound according to claim 1 of formula IIC, and salts thereof;

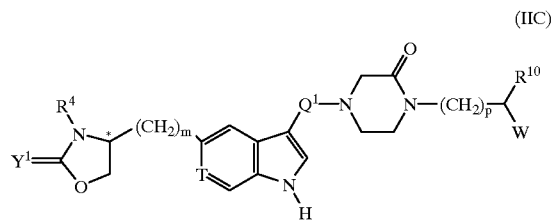

(IIC)

wherein the asterisk * denotes a chiral centre;

m is zero, 1, 2 or 3;

p is zero or 1;

$Q^1$ represents a straight or branched $C_{2-5}$ alkylene chain optionally substituted in any position in a hydroxy group;

W represents a group of formula (Wa);

(Wa)

in which $W^1$ represents CH;

$R^9$ represents hydrogen or fluoro; and $R^{10}$ represents hydrogen or methyl, with the proviso that $R^9$ cannot represent fluoro when p is zero and $R^{10}$ represents hydrogen or when p is 1 and $R^{10}$ represents methyl;

and $R^4$ and $Y^1$ are as defined in claim 1.

6. A compound as claimed in any one of claims 3 to 5 wherein $R^{10}$ represents hydrogen or methyl.

7. A compound as claimed in claim 6 wherein $R^{10}$ is hydrogen.

8. A compound selected from:

1-benzyl-4-[3-(5-(1,2,4-triazol-4-yl)-1H-indol-3-yl)propyl]piperazin-2-one;

1-(2-phenylethyl)-4-[3-(5-(1,2,4-triazol-4-yl)-1H-indol-3-yl)propyl]piperazin-2-one;

1-[2-(3-fluorophenyl)ethyl]-4-[3-(5-(1,2,4-triazol-4-yl)-1H-indol-3-yl)propyl]piperazin-2-one;

and salts thereof.

9. A compound selected from:

1-[2-(3,4-difluorophenyl)ethyl]-4-[3-(5-(1,2,4-triazol-4-yl)-1H-indol-3-yl)propyl]piperazin-2-one;

1-benzyl-4-[3-(5-(1,2,4-triazol-4-yl)-1H-indol-3-yl)propyl]piperazin-2-thione;

1-(2-phenylethyl)-4-[3-(5-(1,2,4-triazol-4-yl)-1H-indol-3-yl)propyl]piperazin-2-one;

1-[2-(3-fluorophenyl)ethyl]-4-[3-(5-(1,2,4-triazol-4-yl)-1H-indol-3-yl)propyl]piperazin-2-one;

and salts thereof.

10. A compound selected from:

1-(2-phenylpropyl)-4-[3-(5-(1,2,4-triazol-4-yl)-1H-indol-3-yl)propyl]piperazin-3-one;

and salts.

11. A pharmaceutical composition comprising a compound of formula I as defined in claim 1 or a pharmaceutically acceptable salt thereof in association with a pharmaceutically acceptable carrier.

12. A method for the treatment and/or prevention of migraine, cluster headache, chronic paroxysmal hemicrania, headache associated with vascular disorders, tension headache, and paediatric migraine, which method comprises administering to a patient in need of such treatment an effective amount of a compound of formula I as defined in claim 1, or a pharmaceutically acceptable salt thereof.

* * * * *